US 6,616,653 B2

(12) United States Patent
Beyar et al.

(10) Patent No.: US 6,616,653 B2
(45) Date of Patent: Sep. 9, 2003

(54) METHOD AND APPARATUS FOR COAGULATION OF SUPERFICIAL BLOOD VESSELS IN BLADDER AND PROXIMAL URETHRA

(75) Inventors: Mordechai Beyar, Caesarea (IL); Nathan Klugman, Jerusalem (IL)

(73) Assignee: American Medical Systems, Inc., Minnetonka, MN (US)

( * ) Notice: Subject to any disclaimer, the term of this patent is extended or adjusted under 35 U.S.C. 154(b) by 0 days.

(21) Appl. No.: 09/834,473

(22) Filed: Apr. 13, 2001

(65) Prior Publication Data

US 2002/0042608 A1 Apr. 11, 2002

Related U.S. Application Data

(60) Provisional application No. 60/197,141, filed on Apr. 14, 2000.

(51) Int. Cl.[7] ................................................. A61B 18/18
(52) U.S. Cl. ............................. 606/14; 606/15; 607/88; 607/89; 607/92
(58) Field of Search ................................. 606/14–15, 2, 606/3, 16, 27; 607/88, 89, 92, 100, 113; 392/408

(56) References Cited

U.S. PATENT DOCUMENTS

| 4,313,431 A | * | 2/1982 | Frank .......................... 606/45 |
| 4,539,987 A | | 9/1985 | Nath et al. |
| 4,627,435 A | * | 12/1986 | Hoskin ......................... 606/28 |
| 4,760,840 A | | 8/1988 | Fournier, Jr. et al. |
| 5,125,925 A | | 6/1992 | Lundahl |
| 5,342,353 A | * | 8/1994 | Allen ........................... 606/14 |
| 5,405,368 A | | 4/1995 | Eckhouse |
| 5,437,660 A | | 8/1995 | Johnson et al. |
| 5,451,221 A | * | 9/1995 | Cho et al. ...................... 606/3 |
| 5,487,740 A | | 1/1996 | Sulek et al. |
| 5,531,739 A | * | 7/1996 | Trelles ......................... 606/2.5 |
| 5,549,600 A | * | 8/1996 | Cho ............................. 606/15 |
| 5,593,404 A | * | 1/1997 | Costello et al. ................ 606/15 |
| 5,685,824 A | * | 11/1997 | Takei ........................... 600/135 |
| 6,152,919 A | * | 11/2000 | Hakky .......................... 606/15 |
| 6,254,601 B1 | * | 7/2001 | Burbank et al. ............... 606/45 |
| 6,375,651 B2 | * | 4/2002 | Grasso, III et al. ........... 606/15 |

FOREIGN PATENT DOCUMENTS

| CA | 2198826 | * | 8/1998 |
| DE | 2852653 | * | 6/1982 |
| DE | 3600713 | * | 7/1986 |
| DE | 3600730 | * | 7/1986 |
| JP | 11-276499 | * | 10/1999 |
| WO | 93/25136 | * | 12/1993 |
| WO | WO 98/22034 A2 | | 5/1998 |
| WO | WO 98/22184 A1 | | 5/1998 |
| WO | 00/15131 | * | 3/2000 |

OTHER PUBLICATIONS

Frank, F., et al., "Various Effects of the CO2–, the Neodymium–YAG–, and the Argon–Laser Irradiation on Bladder Tissue," Lasers in Surgery & Med. 2:89–96 (1982).*
Hofstetter, A., "Applications of Lasers in Bladder Cancer," Seminars in Surg. Oncology 8:214–216 (1992).*

* cited by examiner

Primary Examiner—John A. Jeffery
(74) Attorney, Agent, or Firm—Oppenheimer Wolff & Donnelly, LLP; Barbara A. Wrigley

(57) ABSTRACT

An apparatus and method of use are disclosed to treat and/or diagnose urological disorders. The non-implantable device includes a light source housed within a light source segment. The light source segment is of a sufficiently small size and configuration so that it can be inserted through the urethra and positioned adjacent the target site in the patient. Different types of light sources can be used to achieve a variety of energy levels and distributions useful in treating incontinence disorders. Both incoherent and coherent light sources may be used with the present invention. In addition, the light from the light source can be designed to be pulsed or continuous wave and may be in any suitable spectrum, including visible (such as white light) and infrared. The particular characteristics of the light emitted from the light source, such as wavelength, frequency, amplitude, etc., depend upon the particular treatment and procedure.

7 Claims, 6 Drawing Sheets

METHOD AND APPARATUS FOR COAGULATION OF SUPERFICIAL BLOOD VESSELS IN BLADDER AND PROXIMAL URETHRA

CROSS REFERENCE TO RELATED APPLICATIONS

The present application claims priority of U.S. Provisional Application Serial No. 60/197,141, filed Apr. 14, 2000, whose contents are fully incorporated herein by reference.

BACKGROUND OF THE INVENTION

Urinary incontinence, a condition involving involuntary loss of urine, affects millions of people throughout the world. Incontinence is often associated with medical disorders such as decubitus ulcers, urinary tract infections, detrusor hyperactivity and renal failure. In addition to the medical aspects of this condition, the social implications for an incontinent patient include loss of self-esteem, embarrassment, restriction of social and sexual activities, isolation, depression, and, in some instances, dependence on caregivers. As such, many affected patients do not report the problem to their physicians even though incontinence is highly treatable and even curable.

In general, normal continence results when the lower urinary tract, kidneys and nervous system function properly in combination with the patient's ability to recognize and appropriately respond to the urge to urinate. Ordinarily, the process of urination involves two phases. The first phase is the filling and storage phase whereby the bladder begins to fill with urine from the kidneys and stretches to accommodate the increased amount of urine. The ability to fill and store urine requires proper functioning of the sphincter muscle, to control urine output, and detrusor (bladder wall) muscle, to control and stabilize bladder distention. The second phase of urination is the emptying phase. The emptying phase requires simultaneous contraction of the detrusor muscle, to force urine out of the bladder, and relaxation of the sphincter muscle, to allow the urine to pass out of the body.

Continence problems may occur, for example, as a result of weakened pelvic muscles, malfunction of the urethral sphincter, trauma to the urethral area, neurological injury, hormonal imbalance or medication side-effects. In general, there are three types of urinary incontinence: stress incontinence, overflow incontinence and urge incontinence. Stress incontinence is the involuntary loss of urine that occurs due to sudden increases in intra-abdominal pressure resulting from activities such as coughing, sneezing, lifting, straining, exercise and, in severe cases, even simply changing body position. This condition usually occurs when the sphincter or pelvic muscles are weakened, for example by childbirth or surgery.

Overflow incontinence is a constant dripping or leakage of urine caused by an overfilled bladder. This condition often occurs in men due to the prevalence of obstructive prostate gland enlargement or tumor.

Urge incontinence, also termed "hyperactive bladder," "frequency/urgency syndrome" or "irritable bladder," occurs when an individual experiences the immediate need to urinate and loses bladder control before reaching the toilet. Urge incontinence is a common problem that increases with advancing age or results from a kidney or bladder infection.

Detrusor hyperactivity, or urge incontinence, is the second most common cause for urine incontinence and may be found in 10 to 15% of asymptomatic men and women between the ages of 10 to 50. The goal in controlling or eliminating detrusor hyperactivity is to reduce irritation of nerve endings at the bladder wall due to inflammation and decrease detrusor (bladder wall muscle) activity. Current treatment methods include bladder drilling, pharmacotherapy and surgical management.

Various methods of ablating the nerves that innervate the bladder have been used to treat incontinence. However, the most common surgical method for treatment of urge incontinence is bladder augmentation by enterocystoplasty. Augmentation cystoplasty is basically a reconstructive surgery in which a segment of the bowel is removed and used to replace a portion of the diseased bladder. Complications associated with this procedure include the usual complications resulting from major abdominal surgery, such as bowel obstruction, blood clots, infection and pneumonia. Because of the morbidity level, this procedure is generally considered a last resort in an incontinence treatment plan.

As a result, practitioners have continually sought a less invasive method of treating urinary incontinence. In particular, there is a desire to obtain minimally invasive yet highly effective device that can be used with minimal to no side effects. Such a device must be biocompatible, non-toxic and simple to use. In addition, the related treatment methods using the device should reduce pain, infections and post operative hospital stays. Further, the method of treatment should also improve the quality of life for patients.

BRIEF SUMMARY OF THE INVENTION

In view of the foregoing, it is apparent that there is a need for a minimally invasive device for treating urinary incontinence, for example, by reducing detrusor hyperactivity, so as to restore normal continence in a patient. There is also a need to provide a method of using such a device to create the desired continence effect.

With respect to the device of the present invention, in the incoherent light source embodiments, the therapeutic treatment device utilized is similar to the embodiments disclosed in U.S. Pat. No. 5,405,368 to Eckhouse, issued Apr. 11, 1995, prior copending U.S. application Ser. No. 08/508,129, filed Jul. 27, 1995, U.S. application Ser. No. 08/477,479, filed Jun. 7, 1995, U.S. application Ser. No. 08/473,532, filed Jun. 7, 1995, and U.S. application Ser. No. 08/383,509, filed Feb. 3, 1995 (collectively "the Eckhouse applications"), the disclosures of which are hereby fully incorporated herein by reference. In the laser light source embodiment, the treatment device is similar to that of Talmore, as described in U.S. Pat. Nos. 5,344,433 and 5,344,434, the disclosures of which are also hereby fully incorporated herein by reference.

The present invention differs from the Eckhouse and Talmore devices in that the exit area, through which the light emerges from the apparatus, is of a size and configuration such that it can be inserted through the urethra, proximal urethra and even into the bladder. An additional distinction is that the device of the present invention delivers light that can be used to treat bladder blood vessels, as opposed to external skin disorders. The present invention may also utilize any type of selective thermolysis of the superficial bladder vessels for the treatment of the above mentioned pathologies.

In general, the present invention contemplates a non-implantable device for treating urological disorders. The device includes a light source and a light source segment, wherein the light source provides the required therapeutic light to treat urological disorders. In addition, the light source segment houses the light source and is of a sufficiently small size and configuration so that it can be inserted through the urethra of the patient. The non-implantable device may also include a viewing assembly, comprising an eyepiece, steering control knob and a light port, and an elongate portion having one or more lumen extending along the length of the elongate portion. The lumens of the elongate portion, which are in communication with the viewing assembly and light source segment, enable direct visualization and illumination of the target site in the patient.

The present invention also contemplates a method of treating urological disorders which may include the steps of inserting a non-implantable device through the urethra and into the bladder of a patient and positioning a tip of the device adjacent a target site within the bladder. The next steps may include activating the device to selectively deliver light to the target site and, finally, removing the device from the bladder and urethra of the patient.

BRIEF DESCRIPTION OF THE DRAWINGS

Other features and advantages of the present invention will be seen as the following description of particular embodiments progresses in conjunction with the drawings, in which.

DETAILED DESCRIPTION OF THE INVENTION

Figure 1:
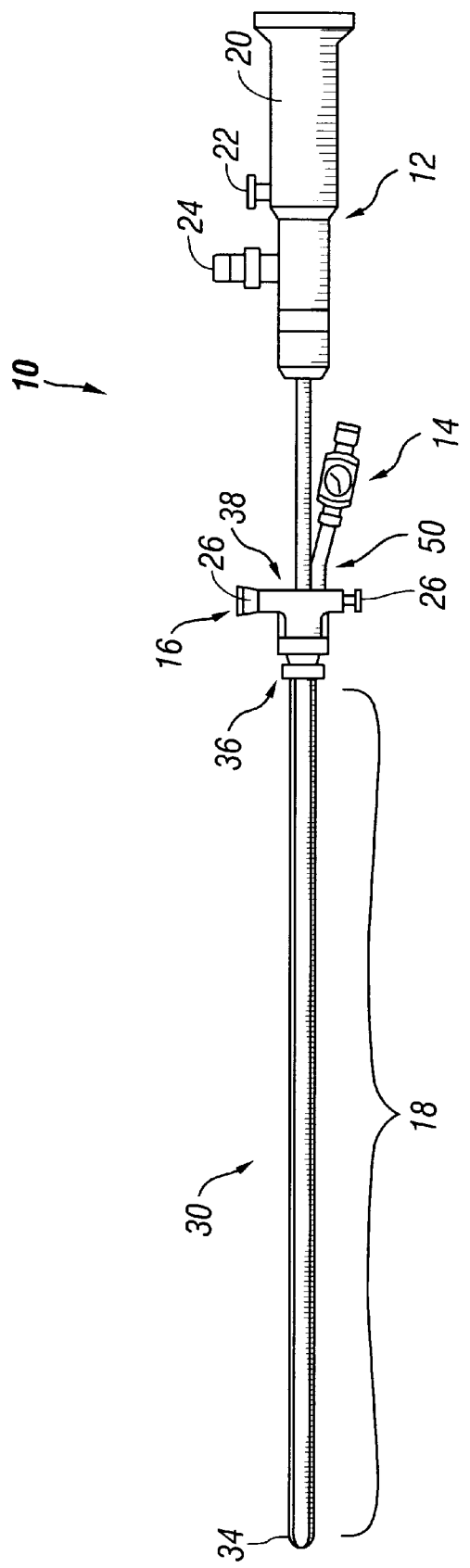
FIG. 1 is a perspective view of an embodiment of the device of the present invention.

Referring to FIG. 1, an embodiment of the non-implantable device 10 in accordance with the present invention includes a light source that emits light used to treat urological disorders. Overall, the device configuration is similar to a cystoscope. Although the invention as disclosed herein generally refers to a cystoscope, other similar devices, such as a urethroscope, catheter or other similar systems, are also included within the scope of the present invention.

In general, the non-implantable device 10 comprises a viewing assembly 12, light source segment 14, delivery/access section 16 and elongate portion 18. The viewing assembly 12 includes an eyepiece 20, a steering control knob or lever 22 and a light port 24. Adjacent to the viewing assembly 12 is the light source segment 14. The light source segment 14 and delivery/access section 16 include a light source (not shown) and one or more ports 26, respectively. Housed within the elongate portion 18 of the device 10 are one or more lumens that extend along the length of the device and are in communication with the above-mentioned components of the viewing assembly 12, light source segment 14 and delivery/access section 16 of the invention. In the spirit of convenience and brevity, the device 10 referenced in the text and figures of the present disclosure is configured according to the above-described design. However, it should be noted that other designs of the device 10 are also within the scope of the claimed invention.

Figure 2:
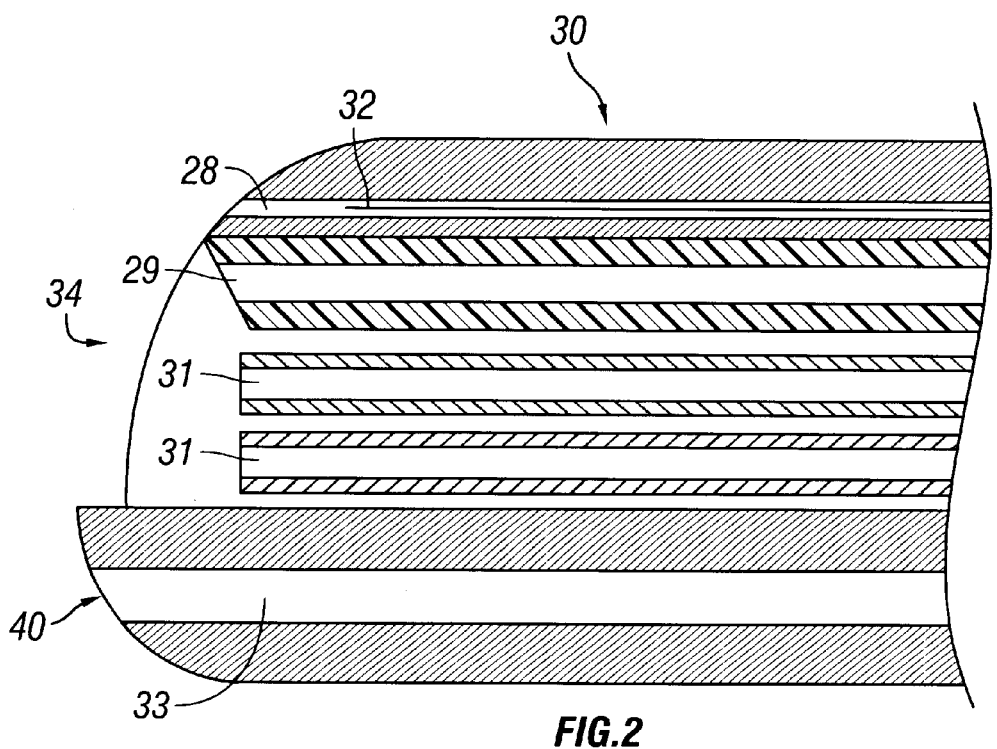
FIG. 2 is a sectional view of an embodiment of the device of the present invention.

The eyepiece 20 and light port 24 of the viewing assembly 12 may be the optical portion of, for example, a standard cystoscope. As shown in FIGS. 1 and 2, these components, together with one or more lumen 28 extending along the length of the device 10, enable direct visualization and illumination of the target site by the operator of the device 10. In an alternate embodiment (not shown), the eyepiece 20 can be replaced with a video device for remote viewing and recording functions.

Imaging of the target site requires locating the distal end 30 of the device at or near the desired target area. The control knob or lever 22 of the viewing assembly 12 functions as the steering mechanism of the device 10. In one embodiment, a guide-wire 32, housed within a lumen 29 and extending along the length of the device 10, is attached to the control knob 22. By manipulating the control knob 22, an operator can steer the distal end 30 of the device 10 through the urethra and position the tip 34 near the target site in the bladder. In an alternate embodiment, a lever 22 and associated guide-wire 32 are used to maneuver the device 10 through the various vessels and organs. The device components and imaging/visualization methods of the present invention as described above are generally known to those skilled in the art and are similar to those used with conventional cystoscopes.

Referring to FIG. 1, the delivery/access section 16 includes one or more ports 26. At least one lumen 31 extends between the ports 26 and the distal end 30 of the device 10. In general, the ports 26 and lumen 31 provide a passageway through which surgical instruments, saline fluid, drugs or other fluids and/or devices can be delivered to the target site. Similarly, tissue samples, fluid samples, implants or related devices or fluids can also be removed from the target area through the ports 26 and associated lumen 28 of the device.

Attached to the distal end 36 of the delivery/access section 16 is the elongate portion 18. The inner diameter of the elongate portion 18 should be large enough to adequately support the various lumens and components housed within the elongate portion 18 of the device 10. Furthermore, the external or outer diameter of the elongate portion 18 should be sized and configured such that it can be easily inserted through the urethra and into the bladder of the patient. In one embodiment, the inner and outer diameters of the elongate portion 18 are approximately within the range of 0.24 to 0.34 inch (0.60 to 0.87 cm) and 0.26 to 0.37 inch (0.67 to 0.93 cm), respectively. In addition, the length of the elongate portion 18 is about 3.94 to 9.84 inches (10 to 25 cm). The segment of elongate portion 18 extending beyond the delivery/access section 16 must be of optimal length, such as that within a range of approximately 7.08 to 7.48 inches (18 to 19 cm), to allow the distal end 30 of the device 10 to access a target site within the bladder of a patient during photodynamic coagulation therapy or a similar procedure.

To minimize potential damage to surrounding tissues when the device is inserted into the body cavity during a procedure, the outer surface of the elongate portion 18 is relatively smooth. Further, since the elongate portion 18 will contact the body, its material should be biocompatible and non-toxic. In a preferred embodiment, the material of the elongate portion 18 is stainless steel. However, other metallic and semi-flexible polymer materials, such as acetal or polytetrafluoroethylene, may also be used. In general, the structure of the elongate portion 18, whether rigid, semi-rigid or flexible, is configured to provide sufficient rigidity to withstand the forces and pressures exerted on it during a medical procedure.

Figure 3:
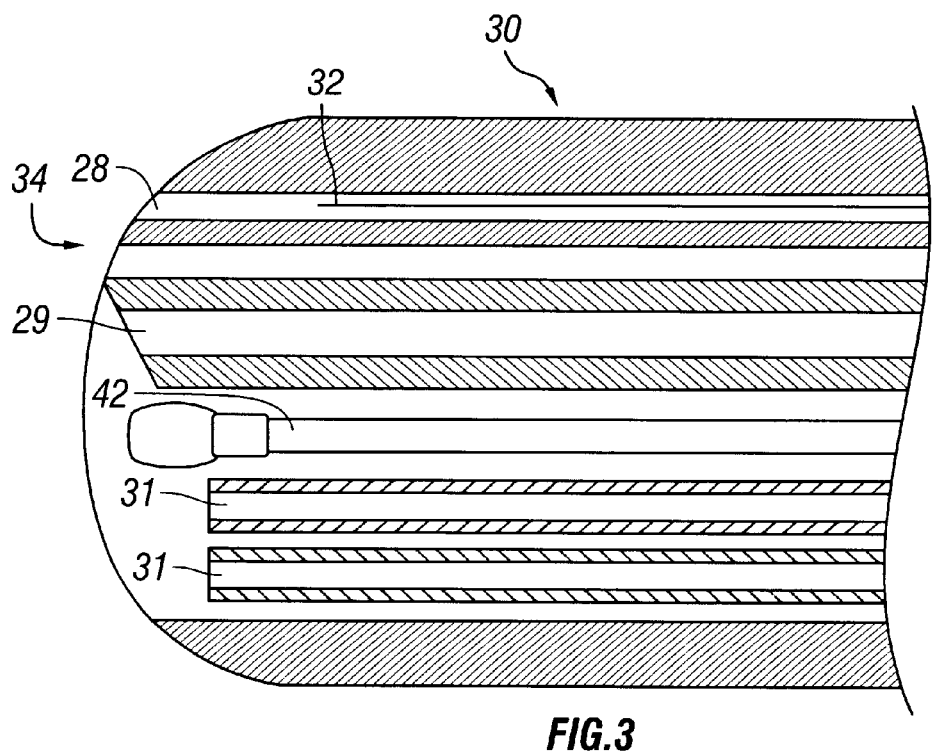
FIG. 3 is a sectional view of another embodiment of the device of the present invention.

Adjacent to the proximal end 38 of the delivery/access section 16 is the light source segment 14. In one embodiment, the light source segment 14 connects to a lumen 33, for example a waveguide lumen, housed within the elongate portion 18 of the device 10. As shown in FIG. 2, the distal end 40 of the waveguide lumen 33 coincides with the tip 34 of the elongate portion 18. In an alternate embodiment, shown in FIG. 3, the light source segment 14 attaches to an optical fiber 42 that is used as a conduit to transmit light from the associated light source (not shown) to the distal end 30 of device. The optical fiber 42 may be movable or fixedly positioned within the elongate portion 18 of the device 10.

The light source segment 14 houses the light source that provides the required therapeutic energy or light to treat incontinence and other related disorders. Alternatively, the light source segment 14 can be used as a connection mechanism that couples the device 10 of the present invention to a separate and/or stand-alone source of light. Different types of light sources can be used so as to achieve a variety of energy levels and distributions useful in treating incontinence disorders. Both incoherent and coherent light sources, such as a flash lamps, toroidal flashlamps, flash tubes, lasers (including holmium, neodynium:yttrium-aluminum-garnet (i.e. Nd:YAG), $CO_2$), arc lamps, light emitting diodes (LED), halogen lamps (such as tungsten halogen lamps) and other light sources may be used. In addition, the light can be pulsed or continuous wave and may be in any suitable spectrum, including visible (such as white light) and infrared. In a preferred embodiment, the device 10 comprises a tungsten halogen lamp light source with an energy dosage of approximately 100 $J/cm^2$. In addition, the light is pulsed at a pulse timing that varies between the range of approximately 1.0 microsecond to 1.0 millisecond. However, the particular characteristics of the light emitted from the light source, such as wavelength, frequency, amplitude, etc., depend upon and can be customized to the particular treatment and procedure.

Based upon the type of light source used and the desired treatment or diagnostic procedure, the light source segment 14 may also include one or more light attenuating devices/components to modify beam profile and intensity. Examples of such components include, but are not limited to, filters, gratings, apertures, knife edges, filter wheels, prisms, pin holes, lenses and other similar devices. The components may be positioned at various locations either internal or external to the light source segment 14. For example, in one embodiment, a filter and lens are housed within the light source segment 14 and located distal to the light source. In an alternate embodiment, a filter and light source are housed within the light source segment 14 and a lens is located at the distal end of the elongate portion 18. In yet another embodiment, the light source segment 14 includes multiple lenses that can be either manually or automatically moved into and out of the beam to modify the spectrum and intensity of light. Other optical components and device configurations, though not specifically described herein, are also included within the scope of the claimed invention.

Figure 4:
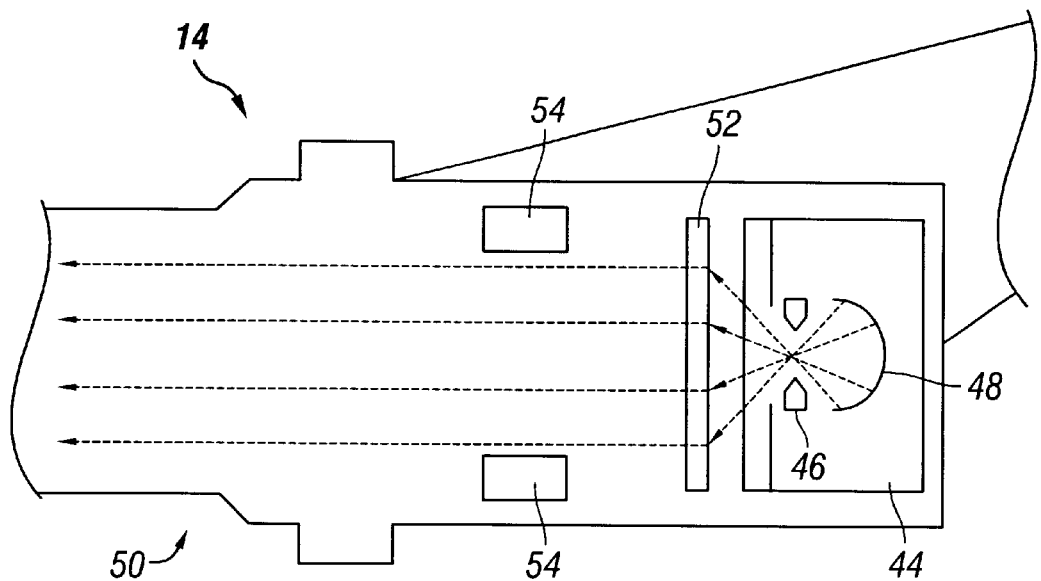
FIG. 4 is a sectional view of an embodiment of the light source segment of the coagulation device.

In another embodiment of the invention shown in FIG. 4, an incoherent light source 44, such as a pulsed flashlamp, is housed within the light source segment 14 of the device 10. The flashlamp assembly comprises an arc lamp 46 and a proximally located reflector 48 used to maximize the energy directed toward the distal end 50 of the light source segment 14. The configuration of the reflector 48 may be parabolic, circular or other related shapes. A filter 52 situated between the flashlamp 46 and distal end 50 of the light source segment 14 transmits a selected application of desired wavelength of light to the target site within the bladder (not shown). In addition, an iris 54 is mounted near the junction of the light source segment 14 and the delivery/access section 16 of the device 10. The iris 54 functions to collimate the output of the flashlamp 46 for delivery through the fiber 42 or lumen 33 of the elongate portion 18 and onto the target site. Thus, the non-implantable device provides controlled density, filtered pulsed light output to the specific area for treatment.

In an alternate embodiment of the invention utilizing an incoherent light source (not shown), a reflector 48 is disposed around the incoherent light source and at least one optical fiber or light guide. The fiber has a first end disposed within the reflector 48 and a second end located at the distal end of the elongate portion 18. The first end of the fiber collects the light from the circular lamp. The light travels through the optical fiber and is emitted from the second end of the fiber onto the target site.

Figure 5:
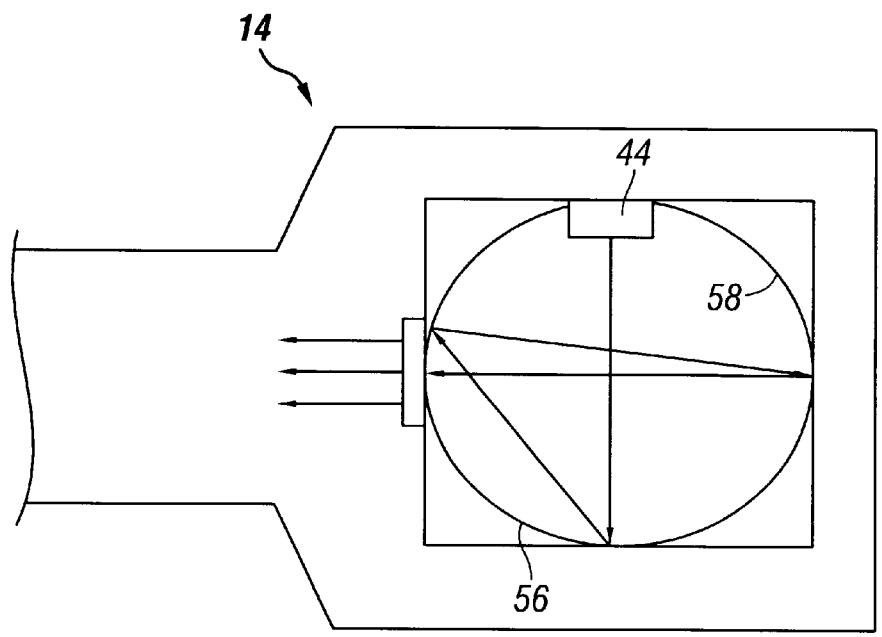
FIG. 5 is a sectional view of another embodiment of the light source segment of the coagulation device.

In another embodiment of the invention, shown in FIG. 5, the light source 44 is any light emitting device housed within or coupled to an integrating sphere 56. The integrating sphere 56 evenly distributes the radiant light uniformly over the entire sphere's inner surface 58. The particular spectral distribution of light exiting the sphere 56 is dependent upon the light source 44 and reflectance of the sphere material. The light spectrum can be tailored to the desired shape by using filters or a variable shutter, as is well known in the art. Further, multiple sources can also be mixed in the sphere 56 to produce a selected uniform output level corresponding to the desired treatment or procedure.

Figure 6A:
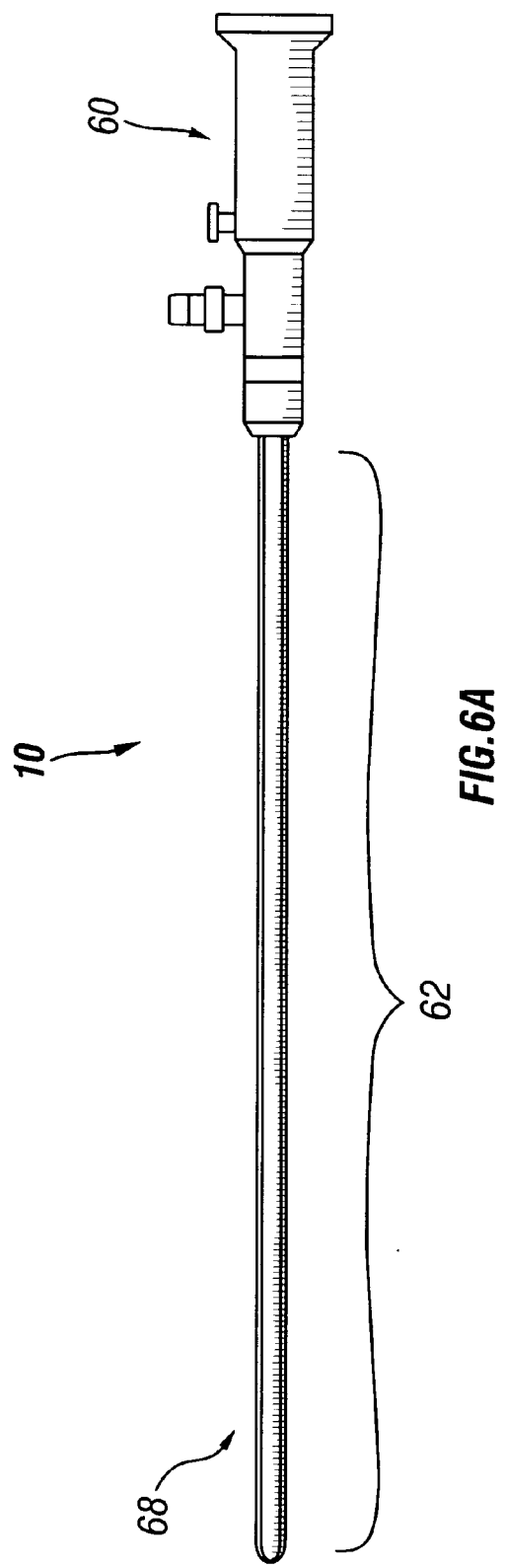
FIG. 6A is a perspective view of another embodiment of the device of the present invention.
Figure 6B:
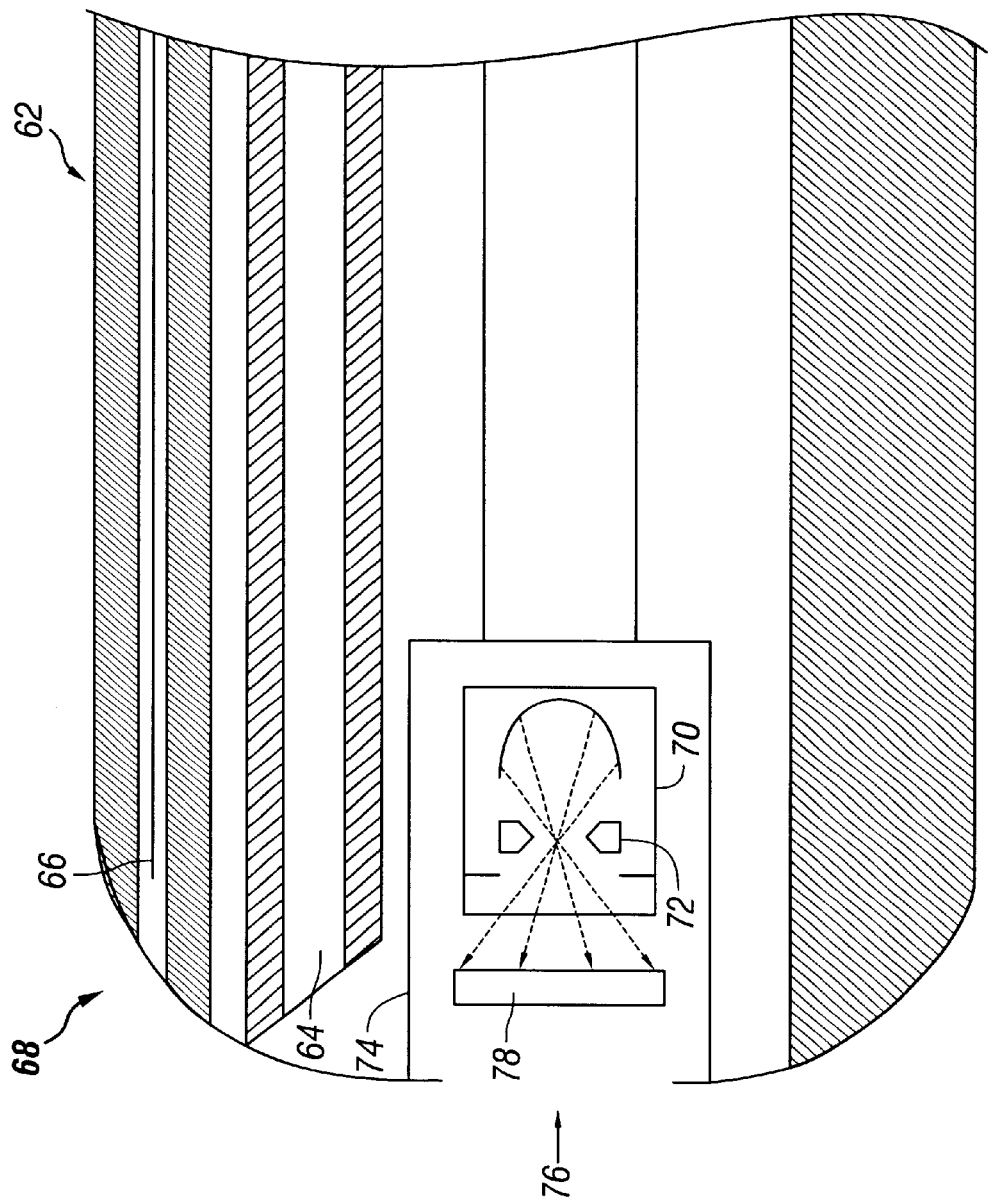
FIG. 6B is a sectional view of another embodiment of the device of the present invention.

In an alternate embodiment, shown in FIGS. 6A and 6B, the non-implantable device 10 comprises a viewing assembly 60 and an elongate portion 62. The viewing assembly 60 is structurally and functionally similar to the viewing assembly 12 detailed above. The elongate portion 62 of the device 10 includes one or more lumen, including a viewing lumen 64 connected to the viewing assembly 62. A steering means, for example a guide wire 66, extends along the length of the elongate portion 62 and is used to maneuver the elongate portion 62 to the target site in the patient. Located at the distal end 68 of the elongate portion 62 is the light source segment 70. The light source segment 70 is of a sufficiently small size and configuration so that it can be inserted through the urethra of the patient. A light source 72 housed within the light source segment 70 delivers light having a predefined wavelength that effectively treats urologic disorders.

Referring to FIG. 6B, the housing 74 of the light source segment 70 includes an opening 76 through which light can be directly transmitted to the treatment site. In addition, a light source 72 and, optionally, a filter 78 are also contained within the housing 74. Depending upon the desired treatment, a variety of light sources 72, filters 78 and other optical components, as previously described, may be used to customize the wavelength of the coagulation device.

Method of Use

Figure 7:
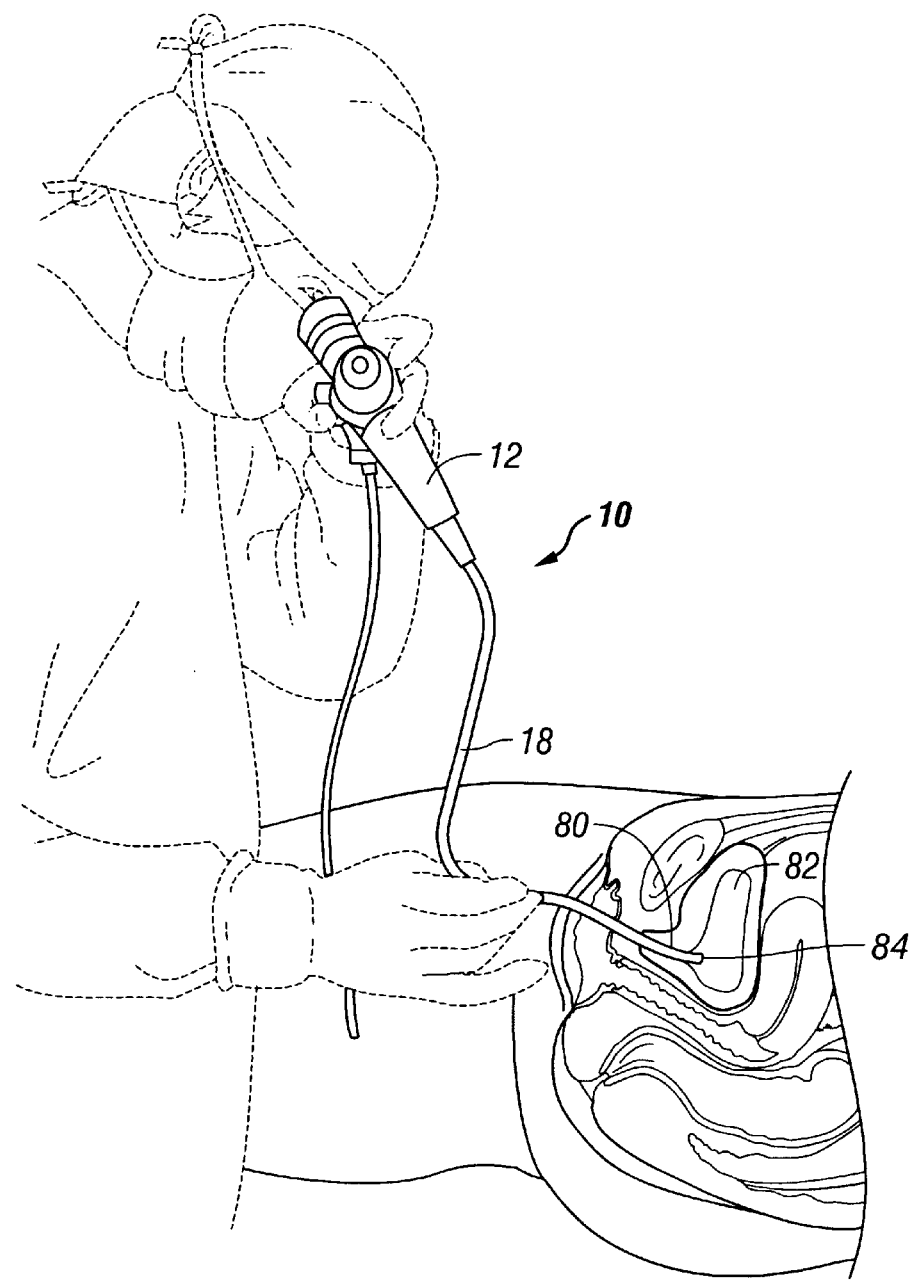
FIG. 7 is a view illustrating an embodiment of the device of the present invention inserted within a patient.

The present invention also contemplates a method of using the non-implantable device 10 to treat incontinence and various urological disorders. The non-implantable device 10 can be utilized for performing both diagnostic and therapeutic procedures. In a preferred embodiment, the elongate portion 18 of the non-implantable device 10 is gently inserted through the urethra 80 and into the bladder 82 of a patient. Referring to FIG. 7, the elongate portion 18 is advanced within the bladder until the tip 84 of the device 10 is positioned near the target site.

Throughout the procedure, the operator of the device 10 uses the viewing assembly 12 to accurately maneuver the device 10 and identify the location of the target site within the bladder. The non-implantable device 10 is positioned adjacent the treatment area such that the tip 84 through which light emerges is sufficiently close to the treatment site. Correct placement of the tip 84 allows light to be precisely focussed onto the desired target site or vessel.

After the tip 84 is properly positioned, the device 10 is then activated to selectively deliver light to the target site. The particular characteristics of the light, such as wavelength, frequency, amplitude, etc., depend upon the desired treatment and procedure. The variable pulsing characteristics and wavelength spectrum of the device 10 allow an operator of the device 10 to customize treatment parameters according to target site location, condition and desired results. Upon completion of the photodynamic treatment, the device 10 is removed from the bladder and urethra of the patient.

In one embodiment, the device 10 of the present invention is used to treat urinary frequency syndrome. Conventional cystoscopy procedures have shown a correlation between proliferation of superficial submucosal bladder vessels of approximately 0.1 mm in diameter, with or without inflammation, and urinary frequency syndrome. Reducing superficial urinary bladder vessels causes reduced bladder hyperemia and associated symptoms, including inflammation. As such, the device 10 of the present invention is used to selectively ablate and, thereby, reduce these vessels. Pulsed unit energy or laser energy in a wavelength that is absorbed by the blood vessels is delivered to the target site according to the above described procedure. Since the light energy is only absorbed by the blood vessels, there is no damage to or significant heating of the surrounding tissue.

In another embodiment, the non-implantable device 10 is used to selectively occlude blood vessels, including bleeding blood vessels, within the urinary tract. This procedure is generally performed in combination with cystopic bladder tumor resection. During cystopic bladder tumor resection, the elongate portion 18 of the device 10 is inserted through the urethra 80 and into the bladder 82 of a patient. The elongate portion 18 is advanced within the bladder 82 until the tip 84 of the device 10 is positioned near the target site/tumor. A type of snare device (not shown) is inserted into a port 26 of the device 10, guided through the elongate portion 18 and positioned adjacent the tumor. The snare device is then manipulated so as to tightly lasso the tumor around the lower stalk of the tumor near the bladder wall. With the snare device properly positioned around the tumor, an electrosurgical current is delivered through the snare device thereby severing the tumor mass from the bladder wall. The snare device and tumor are then withdrawn from the treatment site. To minimize or eliminate post-resection bleeding, the non-implantable device 10 is activated to selectively deliver light to the open blood vessels. As such, light emitted from the non-implantable device 10 selectively coagulates the target vessels, thereby eliminating the need to electrocauterize surrounding tissue. Upon completion of the procedure, the non-implantable device 10 is removed from the bladder 82 and urethra 80 of the patient.

In an alternate embodiment, the non-implantable device 10 may also be used to treat hematuria, i.e. the presence of red blood cells (RBC) in the urine. Hematuria often arises due to diffused small blood vessels bleeding in the superficial mucosa. This condition generally occurs after radiation or systemic chemotherapy or in blood coagulation disorders. Similar to the above-described procedure, the non-implantable device 10 is inserted through the urethra 80 and into the bladder 82. The areas of the bladder wall to be treated are identified via the optics of the device 10. After the distal end of the elongate portion 18 of the device 18 is properly positioned near the target site, photocoagulation of the superficial blood vessels is performed. Upon completion of the procedure, the non-implantable device 10 is removed from the bladder 82 and urethra 80 of the patient.

In another embodiment, the device 10 of the present invention is used to treat detrusor hyperactivity. A method for reducing muscle activity and superficial neural receptors within the bladder wall, especially on the bladder neck, involves reducing the blood supply to these tissues. This is achievable by coagulating the superficial blood vessels that supply blood to the cells. For this procedure, the elongate portion 18 of the non-implantable device 10 is positioned near the target site, i.e. superficial blood vessel, according to the above described method. The device 10 is activated to emit light onto the target site. The wavelength spectrum and pulsing characteristics of the light are customized so that the light is only absorbed by the blood in the vessels. As a result, the hemoglobin, found in red blood cells that flow within the superficial vessels, absorbs the light and reacts to coagulate the blood, thereby blocking the vessels. Thus, the superficial blood vessels are selectively and intravesically coagulated via heat treatment, without causing damage to the surrounding tissue yet resulting in reduced detrusor hyperactivity.

The above described device and procedures can also be used to ablate, occlude or photocoagulate select vessels or target sites for treatment of urethral, prosthetic, ureteral and renal pelvis disorders, such as tumors or transitional cell carcinoma. The preferred method is to directly treat the vessels of interest using light delivered by the non-implantable device 10 of the present invention. In addition, fluids, such as saline, water, chemical agents, etc., or gases may be used in conjunction with the device 10 to alter the treatment method. For example, in cases of active bleeding, elevating bladder pressure by filling the bladder with water may temporarily stop vessel bleeding, allowing easy selective thermolysis of the vessels.

In addition to providing an effective means of treating urological disorders, the device 10 and method of use of the present invention effectively reduce pain, infections and post operative hospital stays. Further, the various treatment methods also improve the quality of life for patients.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of treating urological disorders, comprising:
   inserting a non-implantable device through the urethra and into the bladder of a patient;
   viewing a target site within said bladder using a viewing assembly of said non-implantable device;

positioning a tip of said device adjacent said target site within said bladder; activating said device to selectively deliver light to said target site; said light being absorbed primarily only by blood at said target site; coagulating superficial blood vessels using said light; and removing said device from said bladder and urethra of said patient.

2. The method of claim 1, wherein said tip of said device through which said light emerges is sufficiently close to said target site so as to effect the desired treatment.

3. The method of claim 1 further comprising customizing treatment parameters according to target site location and condition.

4. The method of claim 3 wherein said treatment parameters include variable pulsing characteristics and wavelength spectrum of said device.

5. The method of claim 4 wherein said wavelength spectrum and pulsing characteristics of said light are customized so that said light is only absorbed by blood and reacts to coagulate said blood.

6. The method of claim 1 further comprising ablating said target site using said light.

7. The method of claim 1 wherein said light occludes said target site.

* * * * *